United States Patent [19]

Allgood

[11] Patent Number: 4,668,215

[45] Date of Patent: May 26, 1987

[54] IRRIGATOR-EVACUATOR CONTROL FOR SURGICAL PROCEDURES

[75] Inventor: Fred A. Allgood, Fort Worth, Tex.

[73] Assignee: Dexide, Inc., Fort Worth, Tex.

[21] Appl. No.: 863,437

[22] Filed: May 15, 1986

[51] Int. Cl.[4] .............................................. A61M 1/00
[52] U.S. Cl. ....................................... 604/30; 604/33;
604/236
[58] Field of Search ...................... 604/30, 33, 35, 65,
604/236, 246, 254; 137/625.69

[56] References Cited

U.S. PATENT DOCUMENTS

| | | | |
|---|---|---|---|
| 681,076 | 8/1901 | Porter | 137/625.69 |
| 1,395,469 | 11/1921 | Benbow | 137/625.69 |

Primary Examiner—C. Fred Rosenbaum
Assistant Examiner—J. L. Kruter
Attorney, Agent, or Firm—Richards, Harris, Medlock & Andrews

[57] ABSTRACT

This invention provides an automatic irrigation and evacuation device for use in laparoscopic procedures and surgery. The device comprises a means for directing a flow of liquid and, alternatively, applying a vacuum, through a single line. In the preferred embodiment of this invention, the device provides two different positive controls for alternatively directing a flow of sterile irrigating solution and applying a vacuum through a single line passed through a laparoscope housing into a patient. The two different controls prevent confusion by the operator of the device, increasing the safety of the patient during medical procedures. The invention also optionally includes an external "T" valve attachable to the exterior of the valve body of the present invention to provide convenient connections for a source of carbon dioxide to the laparoscope, surgical laser or both simultaneously.

16 Claims, 10 Drawing Figures

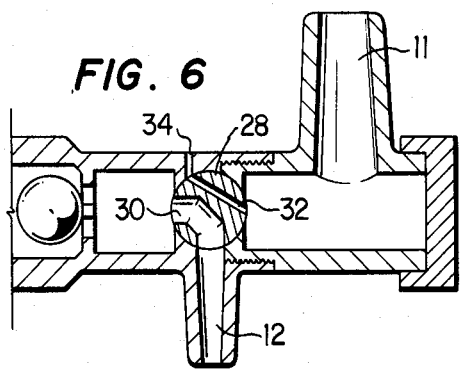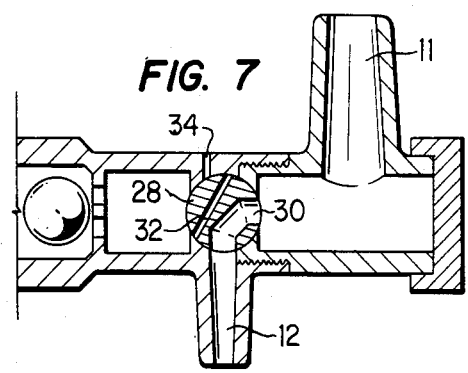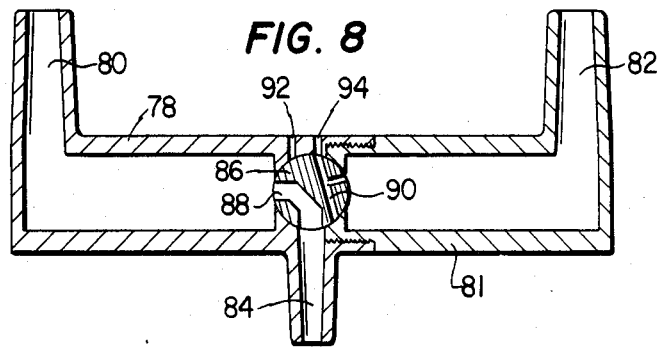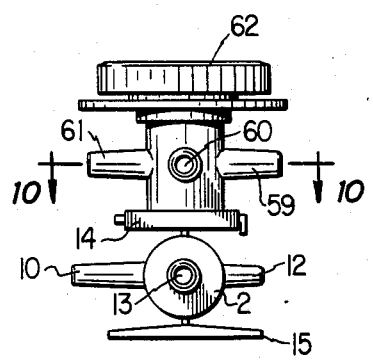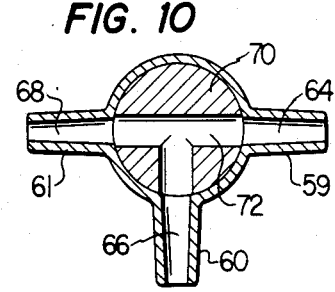

IRRIGATOR-EVACUATOR CONTROL FOR SURGICAL PROCEDURES

TECHNICAL FIELD

This invention relates to medical devices and is more particularly concerned with an automatic irrigating and evacuating device for use in laparoscopic procedures and surgery.

BACKGROUND ART

Development of the laparoscope has given physicians the ability to see inside the body without the necessity of large incisions and their related hazard of infection. Use of the laparoscope, and other related devices, allows the physician to perform a variety of diagnostic and surgical procedures. The scope allows the introduction of microsurgical tools through the scope housing without impeding the physician's vision, permitting simultaneous viewing of the affected area and manipulation of the tools. During these procedures, it is often desirable to irrigate tissues. Following irrigation, or when bleeding occurs, or when smoke is generated by heat or laser evaporation of tissues, it is often necessary to apply a vacuum to evacuate the area of smoke, blood, or irrigating solution to permit continued unobstructed viewing of the area.

In the past, irrigation and evacuation during laparoscopic or other medical procedures was performed by running an individual irrigation tube through the scope housing into the patient and by running an individual vacuum tube from a vacuum source through the scope housing and into the patient, or by using connectors to hook the irrigation tube and the vacuum tube to a single tube to the patient. Until now, the evacuation and irrigation were conducted manually when required, by manipulating pinch clamps placed on the tubes. The disadvantages of this kind of system included the excessive number of lines into the patient reducing the space available in the laparoscopic housing for the passage of other instruments, the time required to assemble the lines and to manually switch from irrigation to vacuum and back, poor control over the amount of vacuum or irrigant from the pinch clamps used on the lines, and the possibility of confusing one pinch clamp with another.

The present invention provides a device which permits both irrigation and vacuum through a single line passed through a laparoscope or similar device. This substantially increases the space available in the laparoscope housing for the passage of other instruments. Additionally, the time required for setting up and performing irrigation and evacuation is significantly decreased, lowering the overall time required for the operation or procedure. Finally, the present invention provides more precise control over irrigation and evacuation.

SUMMARY OF THE INVENTION

The present invention provides a valve device for the convenient connection and control of irrigation solution and vacuum to a patient in laparoscopic surgery. In one embodiment the present invention provides a valve body consisting of a passageway with a first conduit at one end, a second conduit at the other end and a third conduit disposed between the first and second conduit. The first conduit provides an inlet for irrigating solution contained in a reservoir. The second conduit provides for connection to a vacuum source. The third conduit being provided for connection to a line to the patient through which irrigating solution or vacuum is applied. Disposed in the valve body at the junction of the valve body with the third conduit is a "L" valve. The "L" valve having two passageways, an "L" passageway and a vent passageway, and three positions, the first position connects the first conduit and third conduit through the "L" passageway in the valve such that irrigating solution may flow under the force of gravity into the patient while sealing the passageway between the second conduit and third conduit. In this position the vent passage is aligned with a vent hole to permit air to be drawn into the conduit through which vacuum is applied to prevent build up of vacuum. In the second position, the "L" valve provides a passageway between the second conduit and third conduit such that vacuum is applied to the patient while the passageway to the first conduit is sealed thus preventing the further flow of irrigating solution into the patient while vacuum is being applied. In this second position the vent passageway is not aligned with the vent hole. In the third position the "L" passageway does not connect any of the conduits, and is an "off" position. In this third portion the vent passageway is aligned with the vent hole to prevent build up of suction.

In another embodiment the device provides a cylindrical valve body defining a passageway therethrough, a first conduit at one end of the valve body for connection to an aspirator bulb, the second conduit disposed at the other end for connection to a vacuum source, a third conduit disposed between the first and second conduit for connection of a line to the patient; and a fourth conduit located adjacent to the first conduit such that the first conduit is between the fourth and second conduit providing for the connection to an irrigating source. The device further comprises a sealing means disposed between the first conduit and fourth conduit to allow entry of irrigating solution into the valve body but to prevent the flow of irrigating solution from the valve body back to the irrigating solution reservoir. A second sealing means is provided between said first conduit and said third conduit which permits flow of solution into the patient but permits flow in the direction of the first conduit. The device further comprises a valve means for opening and closing the passageway between the second and third conduits such that when the passageway between the second and third conduits is open, vacuum can be applied to the patient and the passageway between the first and third conduits is closed. In a preferred construction of this embodiment a vent is provided such that when the means for opening and closing a passageway between the second and third conduits is positioned such that passageway is closed the vent is opened permitting the flow of air into the vacuum line thus preventing a build up of vacuum.

In the preferred embodiment, the device of the present invention is constructed from a valve body having at one end a first conduit for connecting a line to an aspirator bulb, and at the other end, a second conduit for connecting a line to the vacuum, and a third conduit for connecting a line to the patient. Four ribs which serve as a spring stop and channels for the flow of liquid are also incorporated in the interior middle portion of the valve body. A first solid ball of suitable material is placed inside the valve body and is positioned between the first conduit and the four ribs. An insert having a sealing surface is then fitted into the valve body directly beneath the first conduit, restricting movement of the first solid ball to the space between the sealing surface of the insert and the four ribs, such that a seal is formed when the ball is held against the insert, but not when the ball is held against the four ribs. A second solid ball of suitable material is placed in the insert and a locking connector end cap is placed over the end of the valve body adjacent to the first conduit holding the inserted components in place and providing a fourth conduit for connecting a line to an irrigating solution reservoir. The components and connector end cap are constructed such that a seal is formed when the second ball is held against the fourth conduit but not when the second ball is held against the insert. A spring of suitable material is inserted into the valve body and positioned between the spring stop and the second conduit. A vacuum water seal assembly, comprising a first sealing ring, and a second sealing ring, separated and connected by a rod is inserted into the valve body such that the first sealing ring rests against the spring and in the normal position is positioned between the second and third conduits and the second sealing ring is positioned between the second conduit and the end of the valve body. A plunger is connected to the second sealing ring and protrudes from the end of the valve body and the parts are maintained in place by a locking end cap which fits over the plunger. A vent hole is positioned on the valve body such that the second conduit is between it and the third conduit, and that when the vacuum water seal assembly is positioned to close vacuum off from the patient that the passageway is open from the vent to second conduit to prevent the build up of vacuum.

In operation of the preferred embodiment, a source of irrigating solution is attached to the fourth conduit, a source of vacuum to the second conduit, an aspirator bulb or other suitable device is attached to the first conduit, and the line to patient is connected to the third conduit.

When the vacuum line is attached to the second conduit and a line to the patient is attached to the third conduit, evacuation is accomplished by pressing the plunger into the valve body. This compresses the spring, pushing the first sealing ring beyond the third conduit, opening a passageway between the second conduit and the third conduits applying vacuum to the line to the patient. Evacuation is stopped, when desired, by simply releasing the plunger, which will be pushed back to its normal position by the force of the spring against the first sealing ring, and the vacuum seal assembly will likewise be restored to its initial position with the first sealing ring between the second and third conduits. In this position the vent is open allowing air to be drawn by the vacuum preventing undesired build up of vacuum.

Irrigation may also be performed when tubing to an irrigating solution reservoir is attached to the fourth conduit and tubing to an aspirator bulb is attached to the first conduit. The aspirator bulb is compressed. As the aspirator bulb reinflates, the ball of the first ball valve seals against the insert, closing off the line to the patient. The ball of the second ball valve is pulled against the non-sealing end of the insert and liquid is drawn, by the vacuum created, through channels in the insert around the second ball and through the chamber into the aspirator bulb between the first and second ball valves. When the aspirator bulb is compressed again, the ball of the second ball valve seals against the fourth conduit to prevent the reintroduction of irrigating solution back into the irrigating solution reservoir. The ball of the first ball valve is pushed against the four ribs inside the valve body and the liquid moves around the ball of the first ball valve and down through the third conduit and tubing into the patient where irrigation takes place. The irrigating solution may then be removed from the patient by activating the vacuum as described above.

Other embodiments are possible and some others will be discussed in the detailed description.

In yet another embodiment, the device of the present invention can additionally includes a "T" valve attached to the outside of the valve body to provide a convenient means of connecting a source of carbon dioxide to a surgical laser or to the laparoscope or both simultaneously.

BRIEF DESCRIPTION OF THE DRAWINGS

A better understanding of the invention and its advantages will be apparent from the detailed description taken in conjunction with the accompanying drawing in which:

FIG. 6 is a cross-sectional view of an alternative internal "L" valve;

FIG. 7 is a cross-sectional view of the valve of FIG. 4 in the vacuum position;

FIG. 8 is a cross-sectional view of an optional embodiment of the present invention where the irrigating solution reservoir is elevated and control is exercised by means of a "L" valve;

FIG. 9 is an external side view of the device of the present invention additionally including an external "L" valve; and FIG. 10 is a cross-sectional view of the external "T" valve shown in FIG. 9.

DETAILED DESCRIPTION OF THE INVENTION

The present invention will be described in its preferred embodiment first, followed by some alternate embodiments.

Figure 1:
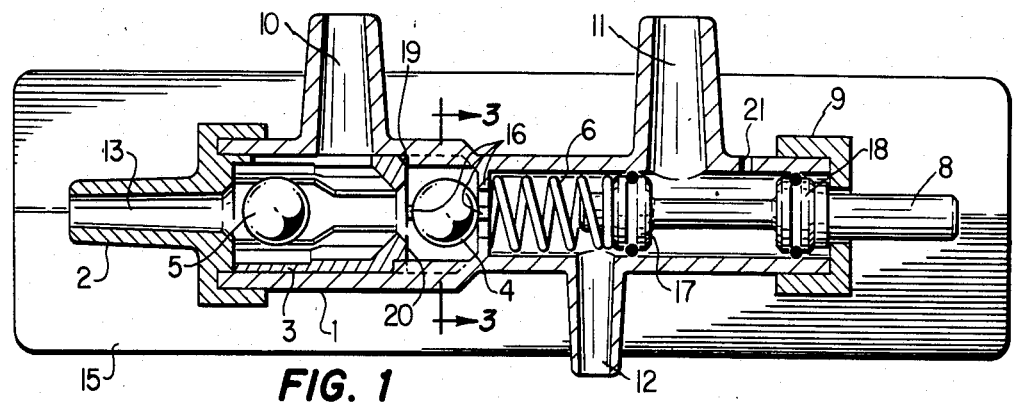
FIG. 1 is a cross-sectional top view of device of the present invention.

FIG. 1 shows a generally cylindrical valve body 1 defining a passageway having one end of larger diameter than the other end and containing a first conduit 10 at the large diameter end and a second conduit 11 and a third conduit 12 at the small diameter end. All conduits extend from the exterior to the interior of valve body 1. In addition to these conduits a vent hole 21 is provided extending from the exterior to interior of the body. Inside valve body 1, at the point where the diameter of the bore changes, are located four ribs 16 which act as a spring stop for the spring 6 which is inserted through the small diameter end of valve body 1 and is seated against the four ribs 16. A vacuum seal assembly, comprising a first sealing ring 17 and a second sealing ring 18 attached to either end of a rod 7, is inserted into the small diameter end of the valve body 1 such that the first sealing ring 17 is seated against the spring and is located, when the spring is not compressed, the vacuum seal assembly is in the normal position between the second conduit 11 and the third conduit 12. When the vacuum seal assembly is in the normal position, the vacuum applied through conduit 11 draws air through vent 21 thus preventing build up of vacuum. Although the vent 21 is not required, it is desirable and preferred. A plunger 8 is attached to the vacuum seal assembly behind the second sealing ring 18, and an end cap 9 is placed over the plunger 8, such that the plunger 8 passes through the end cap 9 and protrudes from the valve body. The end cap 9 is attached to the small diameter end of valve body 1 to hold the small diameter components in place.

Inside the large diameter end of the valve body 1 is located, between the ribs 16 and the first conduit 10, an insert stop 19. A first ball 4 is placed into the valve body 1 through the large diameter end and is freely movable between the insert stop 19 and the ribs 16. An insert 3 containing a sealing end 20 and a non-sealing end is located in the large diameter end of valve body 1 such that the sealing end 20 of insert 3 faces the first ball 4. A second ball 5 is located in the insert 3 and is freely movable between the non-sealing end of the insert and the large diameter end of the valve body. A connector end cap 2 is attached to the large diameter end of the valve body 1 to hold the large diameter components in place, to form a fourth conduit 13 and to form an internal sealing surface for the second ball 5.

Figure 2:
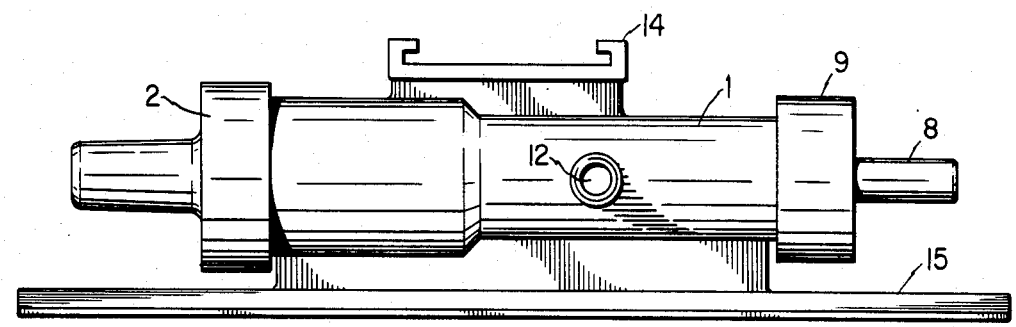
FIG. 2 is an external side view of the device of the present invention.

FIG. 2 shows an exterior side view of the device of the present invention. A bracket 14 and a stand 15 are attached to the exterior of the device. The stand 15 is used to facilitate securing the device to a convenient fixed object before the operation begins, and the bracket 14 is used to attach an optional external "T" valve shown in FIGS. 9 and 10.

The advantages of the present invention over the prior art are significant. Both irrigation and evacuation can be achieved through one tube passed through a laparoscopic or similar device and into a patient. All necessary connections are provided on the device of the present invention. Once the proper connections are made, only two controls, preferably an aspirator bulb or similar device and a plunger need be manipulated to irrigate and evacuate the cavity penetrated by the laparoscopic. A major safety advantage is that once the operator understands that the aspirator bulb controls irrigating, and the plunger controls evacuation, the danger of mistaking one for the other as may occur when multiple lines are used with pinch clamp controls is greatly reduced.

The simplicity of the connections and the ease of operation are apparent from a consideration of FIGS. 1 and 2. Vacuum tubing is attached at one end to a vacuum and at the other end to the second conduit 11. Sterile tubing is connected at one end to an irrigation solution reservoir and at the other end to the fourth conduit 13. An aspirator bulb is connected to the first conduit 10, and when the aspirator bulb is compressed and released, liquid is drawn through the chamber formed by the valve body 1, balls 4 and 5 and end connector 2 into the aspirator bulb and the first ball 4 is suctioned against the insert sealing surface 20. The device can be secured to convenient otjects using tape or claps in conjunctions with the stand 15. Finally, sterile tubing is connected to the third conduit 12 and passed through a laparoscopic or similar device into the patient. When the physician wishes to irrigate the patient he simply compresses the aspirator bulb. This forces the second ball 5 against the connector end cap 2 sealing surface, preventing irrigating solution from being transferred back to the reservoir. The first ball 4 is pushed against the ribs 16 and the liquid is forced around the first ball 4, through the channels between the ribs, through the third conduit 12 and tubing and into the patient. When irrigation is complete, the aspirator bulb is released. As it reinflates, liquid is once again drawn from the reservoir as the second ball 5 moves forward, but does not fill the chamber beyond the insert sealing surface 20 since the first ball forms a seal which is not broken until the aspirator bulb is again compressed.

When evacuation is desired, the physician need only push the plunger 8 into the valve body 1. This moves the first sealing ring 17 against the spring 6, compressing the spring 6 as the first sealing ring 17 slides beyond the third conduit 12, opening a passageway between the vacuum and the patient. The second sealing ring 18 seals the small diameter end of the valve body 1, preventing exposure of the vacuum to the atmosphere by sealing off vent 21 thus avoiding a corresponding reduction in efficiency of the vacuum. When evacuation is complete, the physician need only release the plunger. The spring will force the rest of the vacuum seal assembly outward such that the first sealing ring 17 back at its initial position between the second conduit 11 and the third conduit 12, closing the passageway between the vacuum and the patient. Likewise, the second sealing ring 18 and the plunger 8 will return to their normal positions.

Vent hole 21 is desirable to prevent vacuum surges to the operating area in the patient when the third conduit 12 when the vacuum seal assembly is moved to the evacuation position. Vent hole 21 is not necessary if other means are used to control vacuum surge.

Figure 3:
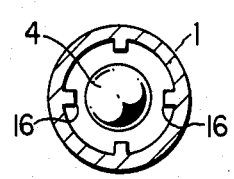
FIG. 3 is a cross-sectional view taken along line 3 of FIG. 1 of the ribs inside the device of the present invention.

FIG. 3 is a cross-sectional view taken along line 11 of FIG. 1. In this view the four ribs 16 are illustrated spacing equally on the inside of the valve body. The first ball 4 is shown in phantom to illustrate the annular channel formed when this first ball is pushed away from the sealing surface 20 by the manipulation of the aspirator bulb.

Figure 4:
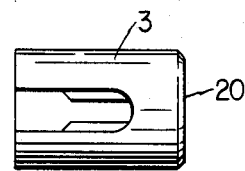
FIG. 4 is an external view of the side of the insert facing inlet 10.

FIG. 4 illustrates the insert 3 and the sealing surface 20 against with first ball 5 seals against. The cutout provided in the insert 3 is aligned with the first conduit 10 so that the conduit is not blocked by the insert.

Figure 5:
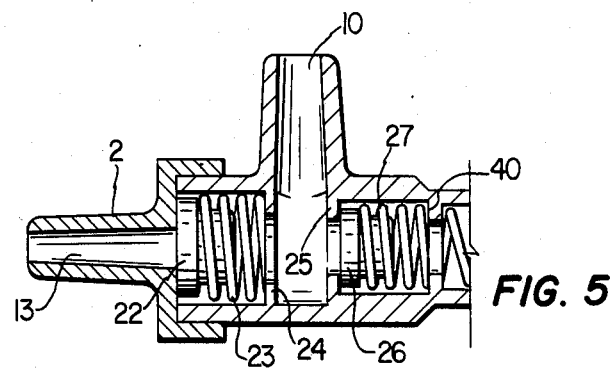
FIG. 5 is a cross-sectional view of a device of the present invention using an alternative sealing arrangement.

Other components can be substituted for the components shown in FIGS. 1–4. For example, FIG. 5 illustrates one alternative arrangement which can be substituted for the ball seals in FIG. 1. In FIG. 5, four ribs 24 are located in the valve body 1 between the first and fourth conduits 13 and 14. A first seal assembly comprising a first seal 22 and a first spring 23 are positioned with the spring against the four ribs 24 (one not shown) and the first seal 22 against the inner sealing surface of the end connector 2 which forms the fourth conduit 13. Spring mount 40 is located inside the valve body 1 between the first 10 and third conduits 12 and a second sealing surface 25 is located between the spring mount 40 and the first conduit 10. A second seal 26 is positioned between the spring mount 40 and second sealing surface 25 with the spring second 27 positioned against the spring mount 40 and the seal 26 against the sealing surface 25. Thus, when the aspirator bulb attached to conduit 10 is compressed and begins to reinflate, the first sealing 22 is suctioned away from the sealing surface on the connector end cap 2 and irrigant is drawn into the valve body and aspirator bulb. When the aspirator bulb is full and suctioning ceases, the spring 23 of the first sealing assembly forces the first seal 22 against the sealing surface of the fourth conduit 13 to prevent liquid from flowing back into the irrigating solution reservoir. When the aspirator bulb is compressed, the second seal 26 of the second sealing assembly is forced back, compressing its spring 27, and liquid flows through the valve body 1 and into the patient through the third conduit 13 (not shown). When the aspirator bulb is fully compressed, the flow of liquid ceases, and the spring 27 of the second sealing assembly forces the seal 26 against the sealing surface 25, and the cycle can be repeated again.

FIG. 6 illustrates an alternative to the vacuum seal assembly illustrated in FIG. 1. In FIG. 6, the opening and closing of passageways between the first 10 and third 13 conduits and beween the second 11 and third conduits 13 is controlled by the use of an externally controlled "L" valve 28 having two positions. In position one, (illustrated) the "L" passageway 30 creates an open passageway between the first 10 and third conduits 13, allowing for flow of irrigant to the patient. In this position the vent passageway 32 contained in valve 28 is aligned with the vent hole 34 in the valve body 1 and to the second conduit 11 to prevent vacuum build up. In this position the passageway between the first conduit 10 and the third conduit 12 is opened such that manipulation of the aspirator bulb will open the seal (either ball 4 or seal 26 depending on the configuration used) and allow irrigating solution to flow into the patient.

FIG. 7 illustrates the valve of FIG. 6 in the second position. In this position the vent 34 is closed off as well as the flow of irrigant. In this second position a passageway is open between the second conduit 11 and third conduit 12 such that vacuum is applied to the patient.

FIG. 8 illustrates a simpler embodiment of the invention also adapted to be used with an elevated irrigating solution reservoir. In this embodiment the first conduit 80 is at one end of the valve body 1 and a second conduit 82 is at the opposite end of the valve body and interposed between them is third conduit 84. A "L" valve 86 is provided at the junction of the third conduit 84, and the valve body 81. The valve 86 contains two passageways, the L passageway 88 and vent passageway 90. In this embodiment, three conduits are required and the passageways between them are controlled by means of a "L" valve 86 having three positions. In position one, a passageway between the second conduit 82 and the third conduit 84 is opened, applying vacuum to the patient. In this position passageway 90 is rotated such that it does not communicate with either vent hole 92 or 94 in valve body 81. In postion two, (illustrated) the valve 86 is rotated such that the L passageway 88 connects first conduit 80 and third conduit 84 allowing irrigant to flow, by force of gravity, into the patient. In this position, the valve is rotated such that the Y shaped vent passageway 90 aligns with a second vent hole 94 to prevent build up of vacuum while the valve is in the closed position. In position three, each conduit is isolated from the other conduits while vent passage 90 aligns with vent hole 92 preventing build up of vacuum. Position three, in essence, is an "off" switch. While gravity flow may be utilized it is not preferred. The ability to use an aspirator bulb to provide variable degrees of force through manipulation of the bulb is beneficial and useful for applying additional force to clean the area around the surgery.

FIGS. 9 and 10 illustrate an additional feature which can be used with any of the embodiments described above. This additional feature comprises an external "T" valve body 56 which may be attached to the valve body 1 at bracket 14 shown in FIG. 9. This "T" valve provides a first connector 59 to which a line to an external source of carbon dioxide gas may be connected, a second connector 60 to which a line to a surgical laser may be connected, and a third connector 61 to which a line to the laparoscope may be connected.

A cross-sectional view of the T valve is shown in FIG. 10 at line 10—10 of FIG. 9. Illustrated are connectors 59, 60, 61 defining passageways 64, 65, and 68 respectively. Rotatable valve stem 70 contains a T shaped passageway 72 which can be aligned to connect all three passages 64, 66, 68 or just two of the passageways 64, 66, 68, or disconnect all the passages. Thus, by rotating the knob 62, the valve the surgeon may selectively apply carbon dioxide from the first connector to the laser, or to the laparoscope, or to both simultaneously.

One skilled in the art will recognize at once that it would be possible to construct this invention from a variety of materials and that the materials should be sterilizable. The present invention can be constructed so that it is either reusable or disposable after one use. Suitable materials include stainless steel and a wide variety of plastics commonly used in the medical field. The sealing rings 17 and 18 may be made of any suitable material which is slidable in the passageway defined by the valve body. For example they may be constructed of a solid disc with a groove provided to accept an O-ring, thus creating a slidable seal. While the preferred embodiment of the present invention and alternative variations thereof have been described in detail, and shown in the accompanying drawings, it will be evident that various further modifications and uses not illustrated are possible without departing from the scope of the invention.

I claim:

1. An apparatus for alternating the passage of an irrigating liquid and the application of vacuum in a surgical procedure comprising:
    (a) a valve body defining a generally cylindrical passageway therethrough;
    (b) a first conduit at one end of said valve body extending from the exterior to the interior of said valve body;
    (c) a second conduit at the second end of said valve body extending from the exterior to the interior of said valve body;
    (d) a third conduit located on said valve body between said first and said second conduits and extending from the exterior to the interior of said valve body;
    (e) a vent extending from the exterior to the interior of said valve body;
    (f) a valve means, located at the junction of said valve body with said third conduit, containing two passageways therein;
        (i) the first passageway being selectively positioned such that said first conduit and said third conduit can be connected while said second conduit is sealed from said first and third conduit, or such that said second and third conduits can be connected while said first conduit is sealed from said second and third conduits, and (ii) said second passageway connects said second conduit and said vent when said first passageway connects said first and third conduits, but seals said vent from said first, second, and third conduits when said first passageway is positioned to connect said second and third conduits.

2. An apparatus for alternating the passage of liquid and the application of vacuum through a single line in a surgical procedure comprising:

(a) a generally cylindrical valve body;

(b) a first conduit at one end of said valve body extending from the exterior to the interior of said valve body;

(c) a second conduit at the other end of said valve body extending from the exterior to the interior of said valve body;

(d) a third conduit located on said valve body between said first and second conduits and extending from the exterior to the interior of said valve body;

(e) a fourth conduit, located adjacent to said first conduit on said valve body such that said first conduit is between said fourth conduit and said second conduit and extending from the exterior to the interior of said valve body;

(f) a first means for sealing the said fourth conduit, located between said first conduit and said fourth conduit in the interior of said body, to permit liquid to flow into said valve body, through said fourth conduit but to prevent liquid from being forced out of said valve body through said fourth conduit;

(g) a second means for sealing the interior position of said valve body containing the said first and fourth conduits from the remaining interior portions of said valve body when a vacuum is applied to the said first conduit, said means being located inside said valve body between said first conduit and said third conduits; and (h) a means for opening and closing the passageway between the said second and third conduits inside said valve body such that when the passageway between said second and third conduits is open the passageway between said first and third conduit is closed.

3. The apparatus of claim 2 wherein said first sealing means is a ball valve.

4. The apparatus of claim 2 wherein said second sealing means is a ball valve.

5. The apparatus of claim 2 wherein said means for opening and closing the passageway between said second and third conduits comprising:

(i) a first sealing ring;

(ii) a connecting rod attached to said first sealing ring;

(iii) a second sealing ring attached to said connecting rod and spaced from said first sealing ring such that said first and second sealing rings can be selectively positioned to enable the sealing of said first and third conduits from said fourth conduit and alternatively seal said first conduit from said second and third conduits while creating a passageway connecting said third and second conduits.

6. An apparatus for controlling irrigation and evacuation during a surgical procedure comprising:

(a) a generally cylindrical valve body defining a passageway therethrough;

(b) a first conduit at one end of said valve body extending from the exterior to the interior of said valve body;

(c) a second conduit at the other end of said valve body extending from the exterior to the interior of said valve body;

(d) a third conduit located on said valve body between said first and second conduits and extending from the exterior to the interior of said valve body;

(e) a fourth conduit, located adjacent to said first conduit on said valve body such that said first conduit is between said fourth conduit and said second conduit and extending from the exterior to the interior of said valve body;

(f) a vent conduit extending from the exterior to the interior of said valve body to prevent build up of vacuum when said third conduit is sealed from the other conduits;

(g) a means for sealing the said fourth conduit, located between said first conduit and said fourth conduit in the interior of said valve body, to permit liquid to flow into said valve body through said fourth conduit but to prevent liquid from being forced out of said valve body through said fourth conduit;

(h) a means for sealing the interior position of said valve body containing the said first and fourth conduits from the remaining interior portions of said valve body when a vacuum is applied to the said first conduit, said means being located inside said valve body between said first conduit and said third conduit; and (i) a means for opening and closing a passageway between the said second and third conduits inside said valve body such that when the passageway between said second and third conduits is open the vent passageway is closed and the passageway between said first and third conduits is closed, and that when said second conduit is sealed from said first, third and fourth conduits, said vent conduit is in communication with said second conduit.

7. The apparatus of claim 6 wherein said first and second means for sealing are check valves permitting one way flow.

8. The apparatus of claim 7 wherein said vent conduit is positioned such that said second conduit is located between said vent conduit and said third conduit.

9. The apparatus of claim 8 wherein said means for opening and closing the passageway between the said second and third conduits comprises:

(i) a first sealing ring, (ii) a connecting rod attached to said first sealing ring, (iii) a second sealing ring attached to said connecting rod and spaced from said first sealing ring to form an annular space in space in said valve body such that said first and second sealing rings can be selectively positioned to enable first position where a passageway is formed between said second conduit and said vent conduit while sealing said first, third and fourth conduits from said second conduit and a second position where a passageway is formed between said second and third conduits while said vent, first and fourth conduits are sealed from said second and third conduits.

10. An apparatus as in claim 6 wherein the said valve body has a large diameter end, a small diameter end, and a middle portion where the large and small diameters merge; four ribs on the inside of the said middle portion of said valve body, a raised ridge on the inside of said valve body between said middle portion and said first conduit, and a sealing surface on the inside of said fourth conduit.

11. An apparatus as in claim 10 wherein the said first conduit is located on the said large diameter end of said valve body, said second conduit is located on the small diameter end of said valve body, said third conduit is located on the said small diameter end of said valve body between and opposing the said first and second conduits, and said vent conduit is located on said valve body such that said second conduit is located between said third conduit and said vent conduit.

12. An apparatus as in claim 11 wherein the said fourth conduit is an end cap attached to the large diameter end of said valve body, and having a sealing surface extending into the interior of said valve body.

13. An apparatus as in claim 12 wherein the said means for sealing the interior portion of said valve body containing the said first and fourth conduits is a ball valve, comprising:
  (a) an insert located inside said valve body between the said large diameter end and the said raised ridge, having a sealing surface at the end abutting the said raised ridge and a non-sealing surface at the end facing said large diameter end of said valve body; and
  (b) a freely moving ball located inside said valve body between the sealing surface of said insert and the said four ribs of the said middle portion of said valve body.

14. An apparatus as in claim 13 wherein the said means for sealing the said fourth conduit is a ball valve comprising a freely moving ball located inside said valve body between said non-sealing surface of said insert and said sealing surface of said fourth conduit.

15. An apparatus as in claim 14 wherein the means for opening and closing the passageway between the said second and third conduits is a slidable vacuum seal assembly comprising:

(a) a spring located inside said small diameter portion of said valve body seated against the said four ribs in the said middle portion of said valve body and extending to a position between said second and said third conduits;
  (b) a sealing ring assembly comprising a first and second sealing ring attached to either end of a rod, located inside the said small diameter end of the said valve body such that the first said sealing ring is seated against said spring between the said second and third conduits, and the said second sealing ring is located between the said second conduit and the said small diameter end of said valve body; and
  (c) a plunger attached to said second sealing ring inside said valve body and protruding from the said small diameter end of said valve body, said assembly being slidable such that said first and second sealing rings can be positioned such that in the first position only said second conduit and said vent conduits are between said sealing rings, and in a second position where only said second and third conduits are between said rings.

16. An apparatus as in claim 6 additionally comprising an external valve assembly for the selection connection two or all three passageways comprising:
  (a) a T valve body attachable to the exterior of said valve body;
  (b) a first connector defining a passageway from the exterior to the interior of the said "T" valve body;
  (c) a second connector defining a passageway from the exterior to the interior of said "T" valve body;
  (d) a third connector defining a passageway from the exterior to the interior of said "T" valve body;
  (e) a valve means rotatable within said T valve body and defining therein a "T" shaped passageway rotatable between said first, second, and third connectors; and
  (f) a knob connected to said valve means for rotating said valve means to selectively align any two or all three of said first second and third connectors or close off all of said first, second and third connectors from each other.

* * * * *